(12) United States Patent
Hertelendy et al.

(10) Patent No.: US 7,135,191 B2
(45) Date of Patent: *Nov. 14, 2006

(54) UROGENITAL OR ANORECTAL TRANSMUCOSAL VACCINE DELIVERY SYSTEM

(76) Inventors: Zsolt Istvan Hertelendy, 3270 Linwood Ave., Cincinnati, OH (US) 45226-1292; Murray Weiner, 8915 Spooky Ridge La., Cincinnati, OH (US) 45242; Michael Howell, 6361 Killerney Ct., Mason, OH (US) 45040; Joseph Thomas, 1654 Grandview Dr., Hebron, KY (US) 41048

( * ) Notice: Subject to any disclaimer, the term of this patent is extended or adjusted under 35 U.S.C. 154(b) by 0 days.

This patent is subject to a terminal disclaimer.

(21) Appl. No.: 09/516,078

(22) Filed: Mar. 1, 2000

(65) Prior Publication Data

US 2003/0138455 A1 Jul. 24, 2003

Related U.S. Application Data

(63) Continuation-in-part of application No. 08/923,813, filed on Sep. 4, 1997, now Pat. No. 6,099,853.

(51) Int. Cl.
*A61K 9/02* (2006.01)
*A61K 39/116* (2006.01)
(52) U.S. Cl. ............... 424/433; 424/203.1; 424/436
(58) Field of Classification Search ............... 424/282, 424/450, 433, 178, 195, 85, 483, 486, 93.1, 424/451, 435, 455, 456, 463, 464, 489, 436, 424/203.1, 244.1, 257.1, 259.1, 475, 480, 424/499; 514/12, 44, 62, 204.1, 449, 2, 951, 514/965, 549; 435/69.1; 523/125; 526/304; 604/8, 870; 536/23.1
See application file for complete search history.

(56) References Cited

U.S. PATENT DOCUMENTS

| | | | | |
|---|---|---|---|---|
| 3,551,554 A * | 12/1970 | Herschler | .................... | 424/9.4 |
| 3,711,602 A * | 1/1973 | Herschler | .................... | 424/45 |
| 3,773,929 A * | 11/1973 | Huber et al. | .................... | 514/21 |
| 3,880,991 A * | 4/1975 | Yolles | .................... | 424/432 |
| 4,221,705 A * | 9/1980 | Kondo | .................... | 260/112.5 R |
| 4,360,593 A * | 11/1982 | Konishi et al. | .................... | 435/70 |
| 4,404,144 A * | 9/1983 | Liang | .................... | 260/410.9 R |
| 4,434,159 A * | 2/1984 | Sekine et al. | .................... | 424/178 |
| 4,439,194 A * | 3/1984 | Harwood et al. | .................... | 604/890 |
| 4,462,984 A * | 7/1984 | Mizuno et al. | .................... | 424/78 |
| 4,606,919 A | 8/1986 | Stojkovic et al. | .................... | 424/92 |
| 4,746,508 A * | 5/1988 | Carey et al. | .................... | 424/278.1 |
| 4,756,907 A * | 7/1988 | Beck et al. | .................... | 424/85 |
| 4,820,698 A | 4/1989 | Degenhardt et al. | .................... | 514/102 |
| 4,849,227 A * | 7/1989 | Cho | .................... | 424/498 |
| 4,863,900 A * | 9/1989 | Pollock et al. | .................... | 514/12 |
| 4,873,090 A * | 10/1989 | Clancy | .................... | 424/451 |
| 4,894,237 A * | 1/1990 | Bellani et al. | .................... | 424/486 |
| 4,939,284 A | 7/1990 | Degenhardt | .................... | 558/142 |
| 5,002,771 A * | 3/1991 | Purkaystha et al. | .................... | 424/433 |
| 5,057,520 A | 10/1991 | Chu et al. | .................... | 514/300 |
| 5,057,523 A | 10/1991 | Chu et al. | .................... | 514/312 |
| 5,096,940 A * | 3/1992 | Mor | .................... | 523/125 |
| 5,149,537 A * | 9/1992 | Azria et al. | .................... | 424/436 |
| 5,189,066 A * | 2/1993 | Kelm et al. | .................... | 514/678 |
| 5,270,344 A * | 12/1993 | Herman | .................... | 514/725 |
| 5,336,666 A * | 8/1994 | Neway et al. | .................... | 424/282.1 |
| 5,364,879 A | 11/1994 | Herman | .................... | 514/452 |
| 5,449,520 A * | 9/1995 | Frigerio et al. | .................... | 424/436 |
| 5,466,463 A * | 11/1995 | Ford | .................... | 424/433 |
| 5,514,670 A * | 5/1996 | Friedman et al. | .................... | 514/2 |
| 5,639,473 A * | 6/1997 | Grinstaff et al. | .................... | 424/450 |
| 5,679,360 A * | 10/1997 | de Lacharriere et al. | ... | 424/401 |
| 5,681,552 A * | 10/1997 | Shevade et al. | .................... | 424/65 |
| 5,681,811 A * | 10/1997 | Ekwuribe | .................... | 514/8 |
| 5,712,257 A * | 1/1998 | Carter | .................... | 514/44 |
| 5,733,540 A * | 3/1998 | Lee | .................... | 424/93.1 |
| 5,776,921 A * | 7/1998 | Gates et al. | .................... | 514/167 |
| 5,783,194 A * | 7/1998 | Brown et al. | .................... | 424/211.1 |

(Continued)

FOREIGN PATENT DOCUMENTS

EP 0486959 * 5/1992

(Continued)

OTHER PUBLICATIONS

Uehling, David T. et al, The Journal of Urology, vol. 157, pp. 2049-2052, Jun. 1997.*

(Continued)

*Primary Examiner*—Lynette R. F. Smith
*Assistant Examiner*—Ginny Allen Portner
(74) *Attorney, Agent, or Firm*—Davidson, Davidson & Kappel, LLC

(57) ABSTRACT

The invention is directed to a suppository based vaccine delivery system for immunizing against urogenital and anorectally transmitted infectious disease in humans and animals and a method for treating the same. More particularly, this invention is directed to a suppository based vaccine delivery system for the prophylaxis against or treatment of urogenital or anorectal transmitted infectious diseases, such as from viral or microbial pathogens. The suppository based delivery system comprises vaccine and/or vaccine adjuvant(s) comprised of whole or fractionated viral or other microbial pathogens, or their purified cellular constituents, whether native, mutated, synthetic, cloned or recombinantly expressed, that consists of nucleic acids, proteins, lipids or other antigenic determinants capable of producing humoral or cellular-mediated immunity in humans or animals; and a polyethylene glycol base; wherein the suppository is adapted to be inserted into a bodily orifice of a human or animal so as to allow the suppository to be in contact with tissue of the bodily orifice to facilitate transfer of vaccine or vaccine adjuvant(s) material therethrough.

4 Claims, No Drawings

U.S. PATENT DOCUMENTS

| | | | | |
|---|---|---|---|---|
| 5,840,318 | A * | 11/1998 | Marshall et al. | 424/282.1 |
| 5,840,771 | A * | 11/1998 | Oldham et al. | 514/2 |
| 5,853,767 | A * | 12/1998 | Melman | 424/659 |
| 5,854,224 | A * | 12/1998 | Lockett et al. | 514/44 |
| 5,858,371 | A * | 1/1999 | Singh et al. | 424/195.1 |
| 5,858,401 | A * | 1/1999 | Bhalani et al. | 424/450 |
| 5,906,922 | A * | 5/1999 | Whittaker et al. | 435/69.1 |
| 5,908,845 | A * | 6/1999 | Segev | 514/263.21 |
| 6,046,179 | A * | 4/2000 | Murch et al. | 514/62 |
| 6,099,853 | A * | 8/2000 | Hertelendy et al. | 424/433 |
| 6,121,313 | A * | 9/2000 | Gao et al. | 514/459 |
| 6,121,317 | A * | 9/2000 | Wu et al. | 514/530 |
| 6,136,336 | A * | 10/2000 | Tanaka et al. | 424/434 |
| 6,159,174 | A * | 12/2000 | Oldham et al. | 602/77 |
| 6,174,532 | B1 * | 1/2001 | Campo et al. | 424/204.1 |
| 6,200,590 | B1 * | 3/2001 | Eley | 424/433 |
| 6,218,147 | B1 * | 4/2001 | Lingwood | 435/69.3 |
| 6,294,192 | B1 * | 9/2001 | Patel et al. | 424/451 |
| 6,306,993 | B1 * | 10/2001 | Rothbard et al. | 526/304 |
| 6,309,663 | B1 * | 10/2001 | Patel et al. | 424/450 |
| 6,348,583 | B1 * | 2/2002 | Segev | 536/23.1 |
| 6,383,471 | B1 * | 5/2002 | Chen et al. | 424/45 |
| 6,420,425 | B1 * | 7/2002 | Melman | 514/557 |
| 6,531,139 | B1 * | 3/2003 | Gao et al. | 424/400 |
| 6,572,863 | B1 * | 6/2003 | Rovinski et al. | 424/208.1 |
| 6,576,224 | B1 * | 6/2003 | Osbakken et al. | 424/45 |
| 6,576,633 | B1 * | 6/2003 | Young et al. | 514/244 |
| 6,585,980 | B1 * | 7/2003 | Chan et al. | 424/234.1 |
| 6,649,660 | B1 * | 11/2003 | Ninkov | 514/731 |
| 6,660,484 | B1 * | 12/2003 | Charych et al. | 435/7.1 |
| 6,669,951 | B1 * | 12/2003 | Rothbard et al. | 424/436 |
| 6,890,950 | B1 * | 5/2005 | Boothman et al. | 514/454 |
| 2002/0012680 | A1 * | 1/2002 | Patel et al. | 424/400 |
| 2002/0034498 | A1 * | 3/2002 | Smith et al. | 424/93.6 |
| 2003/0044434 | A1 * | 3/2003 | Gao et al. | 424/400 |
| 2005/0020576 | A1 * | 1/2005 | Zhang et al. | 514/217.12 |

FOREIGN PATENT DOCUMENTS

| | | | |
|---|---|---|---|
| WO | 95/11701 | * | 5/1995 |
| WO | 96/07426 | * | 3/1996 |
| WO | 97/03655 | * | 2/1997 |
| WO | 98/44788 | * | 10/1998 |
| WO | 99/31250 | * | 6/1999 |
| WO | 9958726 | * | 11/1999 |

OTHER PUBLICATIONS

Uehling et al, Journal of Urology, vol. 157(6), pp. 2049-2052, Vaginal mucosal immunization for recurrent urinary tract infection:phase II clinical trial.*

Sutjipto, S et al, J of Virology, vol. 64(5), May 1990, p. 2290-2297, Inactivated Simian Immunodeficiency Virus Vaccine failed to protect Rhesus Macaques from Intravenous or Genital Mucosal Infection by delayed disease in Intravenously exposed animals.*

Lacombe, K et al, Vaccine, vol. 23, 2004, pp. 623-628, Risk factors for acellular and whole-cell pertussis vaccine failure in Senegalese children.*

D' Cruz, O.J. et al, Current Pharmaceutical Design, vol. 10, 2004, pp. 315-336, Clinical Development of Microbiocides for the Prevention of HIV infection.*

Orkin, S.H et al, Dec. 7, 1995, Report and Recommendations of the Panel to assess the NIH investment in Research on gene therapy.*

Ellis, Ronald W, Ph.D., New Technologies for making vaccines, chapter 29, pp. 568-575, in Vaccines, W.B. Saunders Company 1988.*

Boslego, John W. et al, Chapter 17, Gonorrhea vaccines, p. 211-223, in Vaccines and Immunotherapy, Pergamon Press, 1991.*

Solco Basle Ltd. Brochure: SolcoUrovac, A Vaccine for the Treatment and Prophylaxis of Chronic Urinary Infections.

Robert F. Service, Medical Research—New Vaccines May Ward Off Urinary Tract Infections, *Science*, vol. 276, p. 533, Apr. 25, 1997.

David T. Uehling, et al., Decreased Immunologic Responsiveness Following Intensified Vaginal Immunization Against Urinary Tract Infection, *The Journal of Urology*, vol. 143, pp. 143-145, Jan. 1990.

David T. Uehling, et al., Urinary Glycosaminoglycan Levels Following Induced Cystitis in Monkeys, *The Journal of Urology*, vol. 139, pp. 1103-1105, May 1988.

Walter J. Hopkins, et al., Local and Systemic Antibody Responses Accompany Spontaneous Resolution of Experimental Cystitis in Cynomolgus Monkeys, *Infection and Immunity*, vol. 55, No. 9., pp. 1951-1956, Sep. 1987.

David T. Uehling, et al., Vaginal Immunization Against Induced Cystitis In Monkeys, *The Journal of Urology*, vol. 137, pp. 327-329, Feb. 1987.

Walter J. Hopkins, et al., In Vitro And In Vivo Adherence of Uropathogenic *Escherichia coli* Strains, *The Journal of Urology*, vol. 135, pp. 1319-1321, Jun. 1986.

David T. Uehling, M.D., Future Approaches to the Management of Urinary Tract Infections, *Urologic Clinics of North America*, vol. 13, No. 4, pp. 749-758, Nov. 1986.

David T. Uehling, et al., A Quantitative In Vivo Assay For Bacterial Adherence To The Urethra, *The Journal of Urology*, vol. 133, pp. 316-318, Feb. 1985.

J. Jensen, et al., Enhanced Immune Response In The Urinary Tract Of The Rat Following Vaginal Immunization, *The Journal of Urology*, vol. 132, pp. 164-166.

D.T. Uehling, et al., Immunization Against Urinary Tract Infections, *Journal d'Urologie*, vol. 91, No. 1, pp. 23-26, 1985.

H. Rüttgers, E. Grischke, Elevation of Secretary IgA Antibodies in the Urinary Tract Immunostimulation for the Pre-Operative Treatment and Post-Operative Prevention of Urinary Tract Infections, *Urologia Internationalis*, vol. 42, No. 6, pp. 1-3, 1987.

E.M. Grischek, et al., Treatment of Bacterial Infections of the Female Urinary Tract by Immunization of the Patients, *Urologia Internationalis*, vol. 42, No. 5, pp. 1-4, 1987.

H. Rüttgers, et. al., Urinary Tract Infections in Women—Current Unsatisfactory Situation and Prospects of a New Therapeutic Concept, *Urologia Internationalis*, vol. 42, No. 5, pp. 1-6, 1987.

D. Kruze, et al., Urinary antibody response after immunisation with a vaccine against urinary tract infection, *Urological Research*, vol. 17, pp. 361-366, 1989.

Mary Crowley, 6 Ways to prevent a bladder infection . . . without giving up sex, *Glamour*.

Curtis & Barnes (editors), Biology (5th ed.), 1989, pp. 356 and 432, Worth Publishers, New York.

* cited by examiner

UROGENITAL OR ANORECTAL TRANSMUCOSAL VACCINE DELIVERY SYSTEM

CROSS REFERENCE TO RELATED APPLICATIONS

This is a continuation-in-part of application U.S. Ser. No. 08/923,813, filed on Sep. 4, 1997, which issued as U.S. Pat. No. 6,099,853 on Aug. 8, 2000.

FIELD OF INVENTION

The present invention relates generally to a system and method for treating disease in humans and animals, specifically a prophylactic treatment of viral or microbial infections in humans or animals. More particularly, the invention relates to a suppository-based, vaccine delivery system for prophylaxis against or therapy for viral or microbial infections in humans or animals, wherein the suppository is intended for transmucosal immunization and is comprised of a vaccine or vaccine adjuvant(s) that is derived from whole or fractionated viral or other microbial pathogens, or their purified cellular constituents or derivatives, whether native, synthetic, cloned or recombinantly expressed, that consists of nucleotide sequences, proteins or other antigenic determinants capable of producing humoral or cellular-mediated immunity in humans or animals. Still more particularly, the present invention relates to a suppository-based, vaccine delivery system for prophylaxis against or therapy for viral or microbial infections in humans or animals, wherein the suppository is used for transmucosal immunization and is comprised of a vaccine or vaccine adjuvant(s) intended for mucosal immunization that is derived from whole or fractionated viral or other microbial pathogens, or their purified cellular constituents, whether native, synthetic, cloned or recombinantly expressed, that consists of nucleotide sequences, proteins or other antigenic determinants capable of producing humoral or cellular-mediated immunity in humans or animals, and wherein the suppository is comprised of a suitable base that liquefies or becomes water miscible at body temperature in order to deliver vaccine components and/or vaccine adjuvant components to the urogenital or anorectal mucosa so as to cause or enhance the development of a desired immune response.

BACKGROUND OF THE INVENTION

Viral and microbial pathogens transmitted through or originating from exposure of the urogenital or anorectal epithelium or mucosa are a major problem in medicine. Urogenital and anorectal structures and systemic tissues beyond may be affected. Such infectious disease can result from mucosal exposure during sexual contact or other contact or from opportunistic growth of the urogenital or anorectal flora.

A tendency for recurrence, reinfection and chronic progression is characteristic of many urogenital or anorectal tract infections. Viral or microbial adherence to the mucosal epithelium is frequently a key precondition for the colonization or infection of these tissues. In-vitro studies have shown that the adherence phenomenon is often accomplished via the pili of bacteria or other outer membrane constituents of infecting viruses or microbes. Such adherence can be prevented by the development of antibodies and/or enhancement of cell-mediated immunity against antigenic components of the invading organisms, which include viruses, bacteria, protozoa, fungi and the like.

Bacteria and viruses are the most frequent causative agents of genitourinary or anorectal tract infections. The genitourinary/anorectal tracts can also be infected by other microorganisms, such as protozoa, fungi and the like. Recurrence and chronicity are characteristic of many genintourinary/anorectal tract infections. Recurrence may be due to either relapse or reinfection.

In spite of a great deal of progress in the treatment of infectious disease, the morbidity and mortality of genitourinary/anorectal tract infections remains unchanged. The reasons for this are myriad and depend on the host susceptibility, heightened sexual exposure and on viral or microbial factors.

Recurrences of infections with a previously infecting organism may result from inadequacy of the treatment administered because of incorrect choice of medicine, emergence of resistance strains, insufficient treatment duration, insufficient concentration of chemotherapeutic agents, the existence of bacterial L-forms, and persistence or survival of viral or microbes in urinary calculi or epithelium of the vaginal or anorectal mucosa and surrounding tissues. Recurrent urogenital/anorectal infections can be reinfections with different strains of organisms responsible for prior infections and generally having a greater capacity to adhere to the epithelial cells of the vagina, urethra or rectum. The reinfecting bacteria can originate in the intestinal flora. Frequently, viruses and chlamydia pathogens may lay dormant in epithelial cells and revert to an active state through mechanisms not fully understood.

The composition of the urogenital or anorectal flora may be altered by chemotherapeutic agents that are used in the treatment and prophylaxis of genitourinary or intestinal infections. The flora frequently develop antibiotic resistance and cause a reinfection or primary opportunistic infection. Such infections may be a consequence of the eradication of normal, harmless flora, such as lactobacilli, allowing other pathogenic microbes, resistant to the antibiotics, to flourish.

Studies have revealed that low levels of secretory IgA (sIgA) in urine indicate a defective local immune response of the urinary tract and favor urogenital tract infections. An important property of sIgA is the prevention of interaction of bacterial pili or outer membrane constituents of viruses or other microbes with the specific receptors found on the epithelium of the vaginal/anorectal mucosa or urinary tract. Pili-mediated adhesiveness is an important virulence factor of the bacteria involved. In the case of viruses and non-piliated microbes, other outer membrane constituents are involved in host-attachment phenomena, prior to propagation to infection. For the defense against infection it is important to reduce the adhesion of the pathogens to the epithelium or to prevent the attachment of the pathogen altogether.

Normally, the host organism forms specific local antibodies against the invading bacteria and secretes these antibodies as sIgA. In patients with persisting or frequently relapsing urinary tract infections this natural mechanism of local immunological infection defense is apparently disturbed. Therefore, enhancement of immune defense is a rational means of eliminating the cause of recurrent urinary tract infections.

A vaccination strategy that stimulates the production of antibodies to a spectrum of antigens that are present in several types of pathogens is desirable. Vaccination of the urogenital or anorectal epithelium with nucleic acids encoding specific proteins involved in pathogen-host attachment phenomena presents a novel method of stimulating cell-mediated immunity.

Previously, vaccines against urogenital infections have been administered parenterally or orally and have resulted in enhanced resistance to urogenital infections. However, patients suffer from side effects such as malaise, fever, and muscle soreness. Oral vaccines are subject to the destructive influences of gastric acidity and digestive enzymes. A necessary retention at a local surface for extended transmucosal contact may be difficult to achieve. Prior art concerning mucosal vaccination through the vaginal route using whole cell lysates has taught enhanced resistance to recurrent infection, but there is no mention of transmucosal immunization by the anorectal route and the production of transmucosal immunity against local infection at the site of delivery system target. No specifically therapeutic local immune response to a delivery system is presented. The efficacy presented is confined to non-specific vaccine materials that present a complex potential to produce complex reactions by poorly understood mechanisms.

In an attempt to overcome the defects associated with parenteral and oral administrations of vaccines or in using vaginally-delivered vaccines comprised of fractionated or whole cell extracts, an intravaginal or intrarectal mucosal vaccine delivery system against infections is proposed wherein the vaccine is comprised of purified antigenic determinants capable of stimulating an immune response to pathogenic factors involved in attachment and disease. Administering a vaccine against urogenital or anorectal infections intravaginally or intrarectally is that there is a mucosal immune system wherein antigens are absorbed through mucosal surfaces and processed by specialized local lymphoid tissues, after which antibodies are secreted onto local mucosal surfaces. In the case of nucleotide vaccines, epithelial cells of the mucosa express the proteins to the cell surface promoting cellular-mediated immune responses. As discussed above, in the genitourinary tract, temporary or partial deficiencies in local vaginal or urinary antibodies are an important factor in the heightened susceptibility to urogenital infections shown in some women. Immunization via the mucosal surfaces within the genitourinary tract is preferable to parental or oral routes as it has been discovered that vaccination via the intravaginal surface creates a secretory immune response in the urogenital tract. With nucleotide vaccines, such vaccination stimulates specific cellular-mediated immune responses.

Advances in the identification of specific pathogenic factors involved in infection attachment and propagation, the elucidation of the mucosal immune system and the ability of the mucosal tissue to participate in cellular-mediated immune response via nucleotide vaccination suggest that vaccination of the genitourinary/anorectal tract by a transvaginal or anal route is preferable to oral or parenteral immunization. The specific method of vaginal or rectal immunization may actually resolve infection before disease ensues, preventing pathogen attachment or neutralizing toxins prior to pathogen and host interaction.

For instance, in the past, urinary tract infections vaccines were administered vaginally in the form of a liquid vaccine. Several problems were associated with the intravaginal administration of liquid urinary tract infections vaccine. The major problem encountered was that the liquid vaccine flowed out of the vagina soon after insertion. This severely limits the amount of time that the liquid antigens are in contact with the mucosal surface of the vagina, decreasing the effectiveness of the vaccine. The antigens need sufficient contact with the vaginal mucous membrane to elicit a secretory immunoglobin response. Patients receiving the vaccination were required to lie in a supine position for an extended time after receiving the vaccine to prevent the vaccine from immediately flowing out of the vagina. However, often the vaccine still leaked out of the vagina following the period of time in the supine position, limiting the effectiveness of the vaccine. In addition, the requirement that patients lie in a supine position for an extended time after receiving the vaccine, is a burden on the patient. Patients may receive several vaccinations over the course of treatment and the patients must spend a considerable amount of time after each vaccination immobile.

U.S. Ser. No. 08/923,813 entitled Vaginal Suppository Vaccine For Urogenital Infections was filed Sep. 4, 1997 and allowed. This application is owned by assignee herein and relates to a suppository based vaccine delivery system for immunizing against urogenital infectious diseases in humans.

It is apparent that improvements are necessary in optimizing vaccine delivery to the urogenital mucosa for effective prophylaxis against urogenital infectious diseases. Further, it is desirable to have a rectally-administered vaccine for effective prophylaxis against rectal tract infections involving transmission through the anorectal tract.

The subject invention overcomes the above limitations and others, and teaches a suppository-based vaccine delivery system for prophylaxis against urogenital and anorectal tract infectious diseases, such as bacterial, protozoal, fungi, viral infections and the like, using fractionated, whole cell or purified protein, nucleic acid or lipid constituents, whether native, mutated, synthetic, cloned or recombinantly expressed, of urogenital/anorectal pathogens that stimulate the generation of humoral or cellular-mediated immune response.

SUMMARY OF THE INVENTION

According to the present invention, there is provided an intravaginally or intrarectally administered suppository based vaccine delivery system for prophylaxis against urogenital or anorectal localized or transmitted infectious diseases.

Further according to the present invention, there is provided a suppository based vaccine delivery system for the prophylaxis against or treatment of urogenitally or rectally transmitted or localized infectious diseases, such as bacterial, protozoal, fungal or viral infections wherein the vaccine or vaccine adjuvant is in contact with the vaginal or anorectal mucous membrane for a sufficient period of time to enhance the immune response.

Still further according to the present invention, there is provided a suppository based vaccine delivery system for the prophylaxis against or treatment of urogenitally or rectally transmitted or localized infectious diseases, such as bacterial, protozoal, fungal or viral infections, wherein the vaccine or vaccine adjuvant is easily administered, does not require the patient to lie in a supine position for an extended period of time after receiving the vaccination, and is suitably administered by the patient for primary and routine booster requirements.

Still further according to the present invention, there is provided a suppository based vaccine delivery system for prophylaxis against urogenitally or rectally transmitted or localized infectious diseases, such as bacterial, protozoal, fungal or viral infections in humans or animals, said suppository comprising: a vaccine or vaccine adjuvant containing whole or fractionated viral or other microbial pathogens, or their purified cellular constituents, whether native, synthetic, cloned or recombinantly expressed, that consists of nucleic acids, proteins, lipids or other antigenic determinants capable of producing humoral- or cellular-mediated immunity in humans or animals, wherein the suppository is comprised of a suitable base that liquefies or becomes water miscible at body temperature in order to deliver vaccine components to the urogenital or anorectal mucosa; wherein the suppository is adapted to be inserted vaginally or rectally so as to allow the suppository to be in contact with mucous membrane to facilitate transfer of vaccine or vaccine adjuvant material therethrough.

An advantage of the present invention is the provision of a suppository based vaccine delivery system for the prophylaxis against or treatment of urogenital and/or rectally transmitted or localized infectious diseases, such as viral or other pathogenic microbial infections, wherein the vaccine or vaccine adjuvant is in contact with the vaginal or rectal mucous membrane for a sufficient period of time to enhance the immune response.

Another advantage of the present invention is the provision of a suppository based vaccine delivery system wherein humoral- and/or cell-mediated stimulation from mucosal vaccination allows immune responses to specifically keep viral or microbial shedding or colonization from occurring or recurring, or prohibiting pathogen-host attachment instead of fighting the infection after it has colonized or has propagated.

Another advantage of the present invention is the provision of a suppository based vaccine delivery system wherein the suppository can be easily manufactured to allow incorporation of vaccine or vaccine adjuvant(s) with preservatives, such as thimersal; is a solid at or below room temperature for structure and to allow ease of insertion; and becomes liquified or water-miscible at body temperature so as to allow its components to enhance an immune response.

Another advantage of the present invention is the provision of a suppository based vaccine delivery system for the prophylaxis against urogenitally or rectally transmitted or localized infectious diseases, such as viral or other pathogenic microorganism infections, wherein the vaccine is easily administered, and does not require the patient to be in a supine position for an extended period of time after receiving the vaccination.

Another advantage of the present invention is the provision of a suppository based vaccine delivery system wherein the vaccine can be readily self-administered by the patient.

Another advantage of the present invention is the provision of a suppository based vaccine delivery system wherein the administration of the vaccine is relatively painless.

Yet another advantage of the present invention is the provision of a suppository based vaccine delivery system wherein the patient may self-administer booster vaccinations periodically. Still other advantages of the invention will become apparent to those skilled in the art upon a reading and understanding of the following detailed description, and appended claims.

DETAILED DESCRIPTION OF THE PREFERRED EMBODIMENT

This invention is directed to a suppository based vaccine delivery system for immunizing against infectious disease in humans and animals and a method for treating the same. More particularly, this invention is directed to a suppository based vaccine delivery system for the prophylaxis against or treatment of urogenitally and anorectally localized or transmitted infectious diseases, such as from viral or other pathogenic microbial infections including but not limited to bacteria, protozoans, fungi and the like. The suppository based vaccine delivery system comprises a vaccine and/or vaccine adjuvant(s) comprising pathogenic microbial or viral antigenic constituents and optionally a preservative and optionally a buffer; wherein the suppository is adapted to be inserted into a bodily orifice of a human or animal so as to allow the vaccine and/or vaccine adjuvant to come in contact with the mucosal tissue of the bodily orifice to facilitate transfer of the suppository material therethrough.

The suppository comprises a vaccine and/or vaccine adjuvant(s) comprising fractionated or whole cell or purified cellular constituents whether native, mutated, synthetic, cloned or recombinantly-expressed pathogenic microbial or viral protein lipids or nucleic acid constituents that are capable of stimulating humoral- or cellular-mediated immune responses against which the pathogens or constituents correspond.

The suppository comprises a vaccine and/or vaccine adjuvant(s) that is prepared by either purifying native pathogen constituents, by synthesis or recombinant expression of protein or genetic components of native pathogens or by purifying synthetic, mutated or cloned pathogen-derived nucleic acid sequences.

The suppository of the present invention comprises any suitable suppository base known in the art. More particularly, the suppository base comprises material that is solid or semi-solid at or below room temperature but liquefies or becomes water-miscible at body temperature. The suppository base includes but is not limited to polyethylene glycol, triglycerides, fatty acids, fatty alcohols, glycerin and the like. Preferably the suppository base is polyethylene glycol. The suppository base optionally includes emulsifying agents such as polysorbate, gelatin, methylcellulose, alginic acid, sodium lauryl sulfate, and the like.

The suppository base is present in the delivery system in any suitable amount so as to allow the incorporation of the vaccine or vaccine adjuvant(s) in a solid or semi-solid form so that the structural integrity is maintained or that insertion into a body orifice can be easily performed. When inserted, the suppository base liquefies or becomes water-miscible at body temperature so as to allow the vaccine and/or vaccine adjuvant components to become in contact with the mucous membrane for a sufficient period of time to enhance the immune response. The weight percent of the suppository base is dependent upon the size of the bodily orifice of the human and/or the animal, the dosage of vaccine and/or vaccine adjuvant(s) necessary to elicit an immune response and its physiochemical characteristics that allow it to remain solid at or below room temperature. The suppository comprises from about 50% to greater than 99%, preferably about 75% to greater than 99% by weight of the suppository base. Preferably the suppository comprises about 75% to about 98% by weight polyethylene glycol. Preferably the suppository comprises about 2% to about 25% by weight polysorbate. The suppository base has a molecular weight in the range of about 400 to about 5000, preferably about 950 to about 3700. In a more preferred embodiment, the polyethylene glycol suppository base is comprised of about 39% by weight of polyethylene glycol having a molecular weight of about (3000) and about 59% by weight of polyethylene glycol having a molecular weight of about 400. A suitable commercially available polyethylene glycol suppository base is POLYBASE, available from Paddock Laboratories, Inc.

The suppository base optionally includes either or both of a preservative(s) and a buffer(s). The preservative is selected from the group consisting of thimersal, benzoic acid, benzoic acid derivatives, benzylkonium, benzylkonium chloride sulfites, quaternary ammonium salts, chlorobutanol and combinations thereof at concentrations ranging from about 0.01% to about 0.5%. The buffers are employed so that the pH of the suppository vaccine remains the same. The buffers used are those known in the art and include, but are not limited to citrate, phosphate, hepes (or their salts) and combinations thereof at a concentration in the range of about 5 milimolar to about 0.5 molar.

The suppository base confers a degree of miscibleness with the mucous membrane surfaces of the vagina or rectum, wherein suspended particles of the vaccine and/or vaccine adjuvant(s) are in contact with such mucous membrane surfaces for a sufficient amount of time to elicit a humoral- or cell-mediated immune response. The suppository base has an adjuvant effect that enhances the immune response by allowing the vaccine to facilitate contact time with the vaginal or anorectal tract mucous membranes, serving as a depot that slowly releases antigen, and by localizing and delivering antigens to immunocompetent cells. The suppository base possesses properties that allow the suppository to be molded in a desirable form and further function as a structural necessity that keeps the suppository in its desired molded form at or below room temperature.

The suppository is allowed to harden in a suppository shell or a mold that forms the desired shape. The suppository is generally stored in the shell until used or is removed from the mold and repackaged. The suppository shell or mold is any shell or mold known in the art suitable for molding or packaging of the suppository. A suitable commercially available laminate suppository shell is a polyvinylchloride polyethylene laminate suppository shell available from Paddock Laboratories, Inc.

The suppository based vaccine delivery system of the present invention is prepared by general techniques known in the art. Typically, the suppository base vaccine delivery system is prepared under a sterile environment. The suppository base is heated in a sterile environment to a temperature in the range of its melting point to liquefy the base. The suppository base is heated for a time sufficient to liquefy it without degrading it.

The vaccine or vaccine adjuvant(s) comprising the whole or fractionated viral or other microbial pathogen, or their purified cellular constituents or derivatives, whether native, mutated, synthetic, cloned or recombinantly expressed, that consist of nucleic acids, proteins, lipids or other antigenic determinants capable of producing humoral- or cullular-mediated immunity is placed in a container containing the liquified suppository base. The vaccine and/or vaccine adjuvant(s) are stirred with the liquid suppository base until a homogeneous suspension is produced. A preservative or adjuvant is added and stirred until a homogeneous suspension is again attained. The suspension comprising the suppository base and the vaccine and/or vaccine adjuvant(s) and preservative is placed into individual laminate suppository shells. The suppository is then cooled at room temperature to allow it to harden. The suppositories are then heat-sealed and stored at refrigerated temperature.

The suppository based vaccine delivery system according to the present invention when inserted into a bodily orifice and allowed to liquify or become water-miscible allows the vaccine to be in contact with the vaginal or rectal tract mucous membrane for a sufficient period of time to enhance the immune response. Further, the suppository based vaccine delivery system according to the present invention allows the incorporation of vaccine, vaccine adjuvant(s) and preservative and is easily administered, does not require the patient to lie in a supine position for an extended period of time after receiving the vaccination, is suitably administered by the patient, is painless, is amenable to routine booster vaccinations and allows a favorable method of antigen delivery to immunocompetent cells through the mucosa.

The present invention is further exemplified in the following example. The example illustrates the effectiveness of the suppository based vaccine delivery system of the present invention. It is understood that the example is only illustrative of preferred embodiments according to the present invention wherein the claims set forth the scope of the present invention.

EXAMPLE

In this example, the HSV-2 gD2 and its complementary DNA are used as representative vaccine candidates for mucosal immunization. This protein is specific to the herpes simplex-2 (HSV-2) virus and represents a major outer membrane constituent of the virus that is implicated in the host-attachment phenomena. Others have demonstrated that this protein is a candidate vaccine to prevent transmission or recurrence of HSV-2. This is based on its antigenicity and, that following parenteral vaccination, it elicits satisfactory immune response based on protection against HSV-2 challenge in animal models. The DNA of HSV-2 gD2 is the cloned complementary DNA encoding this protein. Its use as a DNA vaccine is intended to stimulate the production of cellular-mediated immune response. Both the protein and cDNA is manufactured by Protein Express, Inc., Cincinnati, Ohio.

POLYBASE, a polyethylene glycol polysorbate suppository base manufactured by and available from Paddock Laboratories, Inc., in an amount sufficient to manufacture 50 two-gram suppositories, was heated in a sterile flask atop a magnetic stirrer/heater to a temperature of about 60° C. for about one hour to liquefy the suppository base. Recombinant HSV gD2 protein and/or its complementary DNA, 500 micrograms each (enough to manufacture about 50 suppositories) was aseptically placed in the liquefied suppository base suppository. A sterile magnetic stir bar was placed in the flask, and the vaccine and suppository base were stirred for about 10 minutes at about 60° C. in a temperature-controlled water bath to form a homogeneous suspension. Thimersal, as a preservative, was added to a final concentration of about 0.1% and stirred until a homogeneous suspension was achieved. The suspension comprised of the suppository base, the vaccine and the preservative was then placed into individual polyvinyl chloride-polyethylene laminate suppository shell using a sterile pipette. Approximately 2.0 ml of the suspension was placed into each shell.

The suppository base was cooled at a temperature of about 24° C. for about 30 minutes to harden the suppository base. The top of each shell was heat-sealed and the suppositories were then stored at about 4° C. When used, the suppositories are removed from the shell and inserted vaginally or rectally.

While various embodiments of a suppository based vaccine delivery system for treating or prophylaxes against urogenitally and/or anorectally transmitted or localized infectious diseases and a method for treating or prophylaxes against urogenitally and/or anorectally transmitted infections in humans and animals have been disclosed, it should be understood that modifications and adaptations thereof will occur to persons skilled in the art. Other features and aspects of this invention will be appreciated by those skilled in the art upon reading and comprehending this disclosure. Such features, aspects, and variations and modifications of the reported results and examples are clearly within the scope of the invention where the invention is limited solely by the scope of the following claims.

The invention claimed is:

1. A method for producing an immune response in humans, said method comprising the steps of:
   (a) contacting a suppository with mucosal tissue of a human at and internal to the urogenital orifice, wherein said suppository comprises an immunogen or vaccine adjuvant(s) of microbial pathogens, capable of producing humoral or cellular-mediated immunity against urogenital disease in humans and a suppository base, wherein the suppository base comprises about 98% of polyethylene glycol and about 2% of polysorbate, to facilitate transfer of the immunogen or vaccine adjuvant material therethrough and induce an immune response in the human.

2. The method of claim 1, wherein said suppository further comprises thimersol as a preservative.

3. The method of claim 1, wherein said urogenital orifice is a vagina.

4. The method of claim 1, wherein said urogenital disease is a urinary tract infection.

* * * * *